US00PP15024P3

(12) United States Plant Patent

Miyazaki et al.

(10) Patent No.: US PP15,024 P2
(45) Date of Patent: Jul. 20, 2004

(54) PETUNIA PLANT NAMED 'SUNCHIFFON'

(50) Latin Name: *Petunia hybrida*
Varietal Denomination: Sunchiffon

(75) Inventors: Kiyoshi Miyazaki, Hikone (JP); Kazunari Iwaki, Ohmihachiman (JP); Takuro Ishihara, Youkaichi (JP)

(73) Assignee: Suntory Flowers Limited, Tokyo (JP)

( * ) Notice: Subject to any disclaimer, the term of this patent is extended or adjusted under 35 U.S.C. 154(b) by 31 days.

(21) Appl. No.: 10/327,033

(22) Filed: Dec. 24, 2002

(65) Prior Publication Data

US 2003/0135906 P1 Jul. 17, 2003

(30) Foreign Application Priority Data

Dec. 28, 2001 (JP) ..... 14307

(51) Int. Cl.[7] ..... A01H 5/00
(52) U.S. Cl. ..... Plt./356
(58) Field of Search ..... Plt./356

(56) References Cited

U.S. PATENT DOCUMENTS

| | | | |
|---|---|---|---|
| PP6,899 | P | 7/1989 | Tsuda et al. |
| PP6,914 | P | 7/1989 | Tsuda et al. |
| PP6,915 | P | 7/1989 | Tsuda et al. |
| PP8,489 | P | 12/1993 | Hirabayashi et al |
| PP8,768 | P | 6/1994 | Hirabayashi et al. . |
| PP9,322 | P | 10/1995 | Tachibana et al. |
| PP9,341 | P | 10/1995 | Tachibana et al. |
| PP9,342 | P | 10/1995 | Sakazaki et al. |
| PP9,556 | P | 5/1996 | Tachibana et al. |
| PP9,557 | P | 5/1996 | Suzuki et al. |
| PP9,754 | P | 12/1996 | Suzuki et al. |
| PP10,045 | P | 9/1997 | Rother |
| PP10,278 | P | 3/1998 | Murakami |
| PP10,279 | P | 3/1998 | Murakami |
| PP10,287 | P | 3/1998 | Murakami |
| PP10,310 | P | 3/1998 | Sakazaki |
| PP10,330 | P | 4/1998 | Sakazaki |
| PP10,355 | P | 4/1998 | Murakami |
| PP10,904 | P | 5/1999 | Hansson |
| PP11,006 | P | 7/1999 | Danziger |
| PP11,352 | P | 4/2000 | Murakami |
| PP11,558 | P | 10/2000 | Murakami |
| PP12,101 | P2 | 9/2001 | Sakazaki |

*Primary Examiner*—Bruce R. Campell
*Assistant Examiner*—Michelle Kizilkaya
(74) *Attorney, Agent, or Firm*—Burns, Doane, Swecker & Mathis, L.L.P.

(57) ABSTRACT

Disclosed herein is a new and distinct variety of Petunia plant having a decumbent growth habit and long stems. The Petunia plant has abundant branching, and a great profusion of blooms with the entire plant remaining in bloom for a considerable period of time. The flowers are single and small in size with the petals having a purplish-pink coloration. The base color of the corolla throat is light greenish-yellow on the inside and the outside of the corolla tube is pale yellow. The plant exhibits high resistance to rain, heat, cold and disease.

2 Drawing Sheets

Botanical/commercial classification: *Petunia hybrida*/Petunia Plant.
Varietal denomination: cv. 'Sunchiffon'.

BACKGROUND OF THE VARIETY

The present invention relates to a new and distinct variety of Petunia plant that originated from crossing a seedling named 'Fantasy Pink Morn' (non-patented in the United States) (♀) and a wild-type Petunia plant named '40-1' (♂) (non-patented in the United States and native to Brazil.

The Petunia is a very popular plant that is used for flower bedding and potting in the summer season. There are only a few Petunia varieties which do not have an upright growth habit and which have a high resistance to rain, heat, and diseases. The Petunia plants such as the 'Revolution Purple Pink' variety (U.S. Plant Pat. No. 6,915), the 'Revolution Brilliant Pink' variety (U.S. Plant Pat. No. 6,914), the 'Revolution Brilliant Pink-Mini' variety (U.S. Plant Pat. No. 6,899), and 'Revolution Blue Vein' variety (U.S. Plant Pat. No. 9,322)) are decumbent-type plants having long stems, a low plant height, abundant branching, and a high resistance to heat, rain and disease. However, there are only a few Petunia varieties having a great profusion of flowers, purplish-pink colored flower petals and a high resistance to rain, heat, and diseases. Accordingly, this invention is aimed at obtaining a new Petunia variety having purplish-pink colored petals together with the above features.

In April 1998, crossing of 'Fantasy Pink Morn' as female parent and '40-1' as pollen parent was conducted at the Omi R&D Center, Flower Division, of Suntory Ltd. In January 1999, 120 seedlings were obtained from this crossing. These seedlings were grown in pots in glasshouses and were evaluated. One new variety was selected in view of its decumbent growth habit and its attractive flower color. This seedling was propagated by the use of cuttings beginning in July 1999, and a further evaluation trial was carried out by flower potting and bedding beginning in March 2000, at the Omi R&D Center, Flower Division, of Suntory Ltd. The botanical characteristics of that plant were then examined, using the similar varieties 'Revolution Pink-Mini' and 'Sunpapi' (non-patented in the United States) for comparison. As a result, it was concluded that this new Petunia plant is distinguishable from all other varieties, whose existence is known to us, and that this new plant is uniform and stable in its characteristics. The new variety of Petunia plant of the present invention was named 'Sunchiffon'.

In the following description, the color-coding is in accordance with The R.H.S. Colour Chart of The Royal Horticultural Society, London, England. A color chart based on The Japan Color Standard for Horticultural Plants (J.H.S. Color Chart) is also added for reference.

The main botanical characteristics of the 'Fantasy Pink Morn' variety are as follows:

Plant:
*Growth habit.*—Erect.
*Plant height.*—Approximately 15.5 cm.
*Spreading area of plant.*—Small.
*Blooming period.*—April to July in the southern Kanto area, Japan.
Stem:
*Length.*—Approximately 9.5 cm.
*Thickness.*—Main stem approximately 2.8 mm.
*Pubescence.*—Sparse.
*Branching.*—Medium.
*Length of internode.*—Approximately 2.2 cm.
*Color.*—Light yellow-green (R.H.S. 145C, J.H.S. 3503).
Leaf:
*Shape.*—Elliptic. The apex shape is acute, and the base shape is attenuate.
*Length.*—Approximately 3.2 cm.
*Width.*—Approximately 2.2 cm.
*Color.*—Upper-side color is strong yellow-green (R.H.S. 144A, J.H.S. 3507). Lower-side color is moderate yellow-green (R.H.S. 147B, J.H.S. 3513).
*Pubescence.*—Sparse.
Flower:
*Facing direction.*—Slightly slanted upward.
*Type.*—Single.
*Shape.*—Funnel-shaped, with five fissures.
*Shape of petal tip.*—Obtuse.
*Lobation.*—Medium.
*Waviness of petal.*—Weak.
*Diameter.*—Approximately 4.5 cm.
*Color.*—Petal: deep purplish-pink (R.H.S. 68B, J.H.S. 9205) with pale purplish-pink (R.H.S. 69D, J.H.S. 9501) towards the margin. The base color of the corolla throat: yellowish-white (R.H.S. 159D, J.H.S. 1901). Outside color of the corolla tube: yellowish-white (R.H.S. 159D, J.H.S. 1901).
*Reproductive organs.*—1 normal pistil and 5 normal stamens. Color of pistil is vivid yellow-green (R.H.S. 144B, J.H.S. 3506). Color of the stamens is pale yellow (R.H.S. 158C, J.H.S. 2702).
*Peduncle.*—Approximately 1.0 mm in thickness, and approximately 1.0 cm in length.
*Physiological and ecological characteristics.*—Strong resistance to cold, rain, pests and disease.

The main botanical characteristics of the '40-1' variety are as follows:

Plant:
*Growth habit.*—Decumbent.
*Plant height.*—Approximately 5.5 cm.
*Spreading area of plant.*—Large.
*Blooming period.*—May to August in the southern Kanto area, Japan.
Stem:
*Length.*—Approximately 16.0 cm.
*Thickness.*—Approximately 1.5 mm.
*Pubescence.*—Normal.
*Branching.*—Abundant.
*Length of internode.*—Approximately 1.5 cm.
*Color.*—Light yellow-green (R.H.S. 145C, J.H.S. 3503).
Leaf:
*Shape.*—Elliptic. The apex shape is acute, and the base shape is attenuate.
*Length.*—Approximately 2.7 cm.
*Width.*—Approximately 1.7 cm.
*Color.*—Upper-side color is strong yellow-green (R.H.S. 143A, J.H.S. 3711). Lower-side color is moderate yellow-green (R.H.S. 147B, J.H.S. 3513).
*Pubescence.*—Sparse.
Flower:
*Facing direction.*—Slanted upward.
*Type.*—Single.
*Shape.*—Funnel-shaped, with five fissures.
*Shape of petal tip.*—Round.
*Lobation.*—Shallow.
*Waviness of petal.*—Weak.
*Diameter.*—Approximately 4.1 cm.
*Color.*—Petal: pale purplish-pink (R.H.S. 76D, J.H.S. 8902). Base color of the corolla throat: yellowish-white (R.H.S. 159D, J.H.S. 1901). Outside color of the corolla tube: yellowish-white (R.H.S. 159D, J.H.S. 1901).
*Reproductive organs.*—1 normal pistil and 5 normal stamens. Color of pistil is vivid yellow-green (R.H.S. 144B, J.H.S. 3506). Color of the stamens is yellowish-white (R.H.S. 155D, J.H.S. 2501).
*Peduncle.*—Approximately 1.1 mm in thickness, and approximately 1.8 cm in length.
*Physiological and ecological characteristics.*—Moderate resistance to pests. Strong resistance to rain, cold, heat and diseases.

The main botanical characteristics of similar 'Revolution Pink-Mini' variety used for comparison are as follows:

Plant:
*Growth habit.*—Decumbent.
*Plant height.*—Approximately 20 cm.
*Spreading area of plant.*—Large.
*Blooming period.*—May to August in the southern Kanto area, Japan.
Stem:
*Length.*—Approximately 15 cm.
*Thickness.*—Main stem is approximately 2.5 mm.
*Pubescence.*—Normal.
*Branching.*—Abundant.
*Length of internode.*—Approximately 2.0 cm.
*Color.*—Light yellow-green (R.H.S. 145C, J.H.S. 3503).
Leaf:
*Shape.*—Elliptic. The apex shape is acute, and the base shape is attenuate.
*Length.*—Approximately 5.0 cm.
*Width.*—Approximately 3.0 cm.
*Color.*—Upper-side color is dark olive-green (R.H.S. 137A, J.H.S. 3509). Lower-side color is moderate yellow-green (R.H.S. 147B, J.H.S. 3513).
*Pubescence.*—Normal.
Flower:
*Facing direction.*—Slanted upward.
*Type.*—Single.
*Shape.*—Funnel-shaped, with five fissures.
*Shape of petal tip.*—Round.

*Lobation.*—Shallow.
*Waviness of petal.*—Weak.
*Diameter.*—Approximately 4.5 cm.
*Color.*—Petal: Vivid reddish-purple (R.H.S. 71D, J.H.S. 9206). Base color of the corolla throat is pinkish-white (R.H.S. 69D, J.H.S. 9201). Outside color of the corolla tube is strong purplish-pink (R.H.S. 73B, J.H.S. 9204).
*Reproductive organs.*—1 normal pistil and 5 normal stamens. Color of pistil is vivid yellow-green (R.H.S. 144B, J.H.S. 3506). Color of stamens is yellowish-white (R.H.S. 155D, J.H.S. 2501).
*Peduncle.*—Approximately 1.0 mm in thickness, and approximately 2.0 cm in length.
*Physiological and ecological characteristics.*—Strong resistance to cold, heat, rain and diseases. Moderate resistance to pests.

The main botanical characteristics of similar 'Sunpapi' variety used for comparison are as follows:

Plant:
*Growth habit.*—Decumbent.
*Plant height.*—Approximately 11.5 cm.
*Spreading area of plant.*—Large.
*Blooming period.*—April to September in the southern Kanto area, Japan.
Stem:
*Length.*—Approximately 18.0 cm.
*Thickness.*—Main stem approximately 3.2 mm.
*Pubescence.*—Normal.
*Branching.*—Many.
*Length of internode.*—Approximately 2.2 cm.
*Color.*—Light yellow-green (R.H.S. 145C, J.H.S. 3503).
Leaf:
*Shape.*—Lanceolate. The apex shape is acute, and the base shape is attenuate.
*Length.*—Approximately 6.1 cm.
*Width.*—Approximately 2.7 cm.
*Color.*—Upper-side color is dark olive-green (R.H.S. 137A, J.H.S. 3707). Lower-side color is moderate yellow-green (R.H.S. 147B, J.H.S. 3513).
*Pubescence.*—Normal.
Flower:
*Facing direction.*—Slanted upward.
*Type.*—Single.
*Shape.*—Funnel-shaped, with five fissures.
*Shape of petal tip.*—Obtuse.
*Lobation.*—Shallow.
*Waviness of petal.*—Weak.
*Diameter.*—Approximately 6.0 cm.
*Color.*—Petal: deep purplish-pink (R.H.S. 68B, J.H.S. 9205). Bottom color of the corolla throat: yellowish-white (R.H.S. 159D, J.H.S. 1901). Outside color of the corolla tube: yellowish-white (R.H.S. 159D, J.H.S. 1901).
*Reproductive organs.*—1 normal pistil and 5 normal stamens. Color of pistil is vivid yellow-green (R.H.S. 144B, J.H.S. 3506). Color of stamens is yellowish-white (R.H.S. 155D, J.H.S. 2501).
*Peduncle.*—Approximately 1.4 mm in thickness, and approximately 1.8 cm in length.
*Physiological and ecological characteristics.*—Strong resistance to cold, heat, rain and diseases. Moderate resistance to pests.

SUMMARY OF THE VARIETY

The new Petunia variety named 'Sunchiffon' has a decumbent growth habit, abundant branching and a great profusion of blooms with the entire plant remaining in bloom for a considerable period of time. The flowers are single and small in size. The petal color is purplish-pink. The plant has a high resistance to rain, cold, heat and diseases.

The plants described and depicted herein were propagated by the use of cuttings and were approximately seven months of age. The plants were grown in 30 cm pots and were grown outdoors from April to September and were observed during September. The plants received approximately 100 ppm of nitrogen content fertilizer each week.

BRIEF DESCRIPTION OF THE PHOTOGRAPHS

DESCRIPTION OF THE NEW VARIETY

The botanical characteristics of the new and distinct variety of Petunia plant named 'Sunchiffon' are as follows when observed during September at Koukaichi-shi, Shiga-ken, Japan at an age of approximately seven months.

Plant:
*Growth habit.*—Decumbent.
*Plant height.*—Approximately 18 cm.
*Plant width.*—Approximately 70 to 75 cm.
*Spreading area of plant.*—Large.
*Blooming period.*—Early April to late October in the southern Kanto area, Japan. The plant shape does not change throughout this period. A typical flower commonly lasts approximately 5 days on the plant when experiencing a temperature of approximately 20° C.
Stem:
*Length.*—Approximately 15 cm.
*Thickness.*—Approximately 2.0 mm.
*Pubescence.*—Normal.
*Branching.*—Abundant.
*Length of internode.*—Approximately 2.0 cm.
*Color.*—Light yellow-green (R.H.S. 145C, J.H.S. 3503).
Leaf:
*Shape.*—Slightly ovate. The apex shape is acute, and the base shape is attenuate.
*Length.*—Approximately 4.0 cm.
*Width.*—Approximately 2.8 cm.
*Color.*—Upper-side is moderate olive-green (R.H.S. 146A, J.H.S. 3508). Lower-side is moderate yellow-green (R.H.S. 137C, J.H.S. 3513).
*Thickness.*—Approximately 0.8 mm.
*Texture.*—Smooth.
*Margins.*—Entire.
*Pubescence.*—Sparse.
*Venation.*—Pinnate and R.H.S. 145B in coloration.
Flower:
*Facing direction.*—Upward.
*Type.*—Single.
*Shape.*—Funnel-shaped, with five fissures.
*Shape of petal tip.*—Round.
*Lobation.*—Shallow.
*Waviness of petals.*—Weak.

*Diameter.*—Approximately 4.5 cm.

*Color.*—Petal: moderate purplish-pink (R.H.S. 68C, J.H.S. 9211). The base color of the corolla throat: light yellow (R.H.S. 1D, J.H.S. 2904). Outside color of the corolla tube: pale yellow (R.H.S. 8D, J.H.S. 2903).

Figure 1:
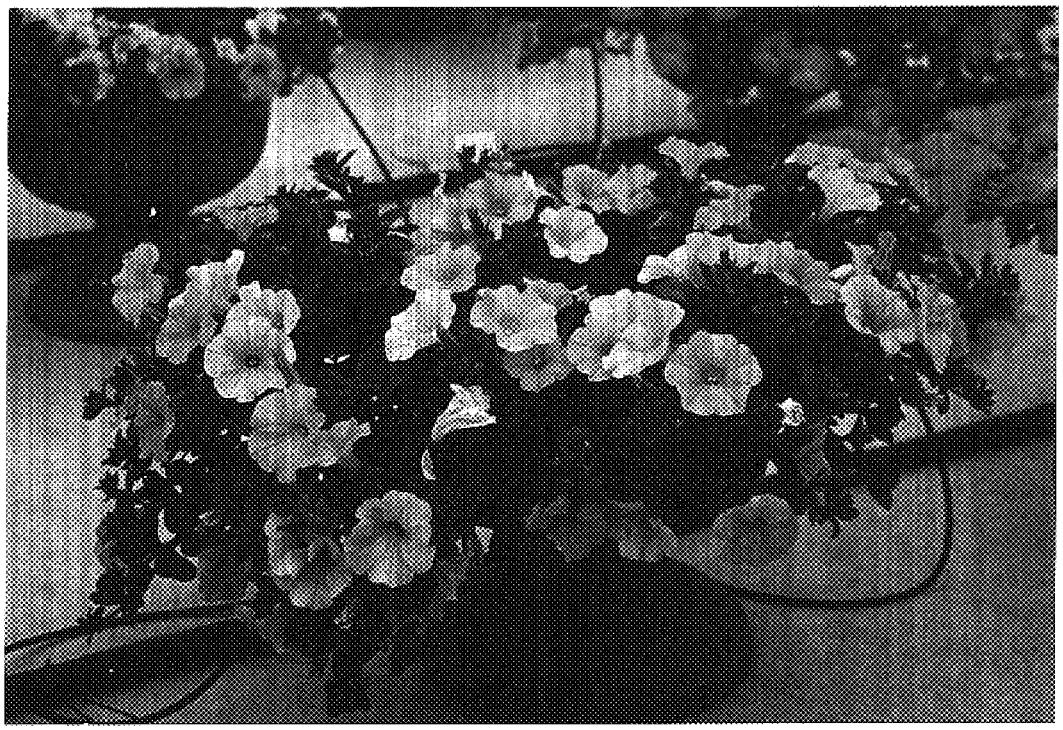
FIG. 1 shows the overall growth habit of the new variety of Petunia plant 'Sunchiffon' while flowering.
Figure 2:
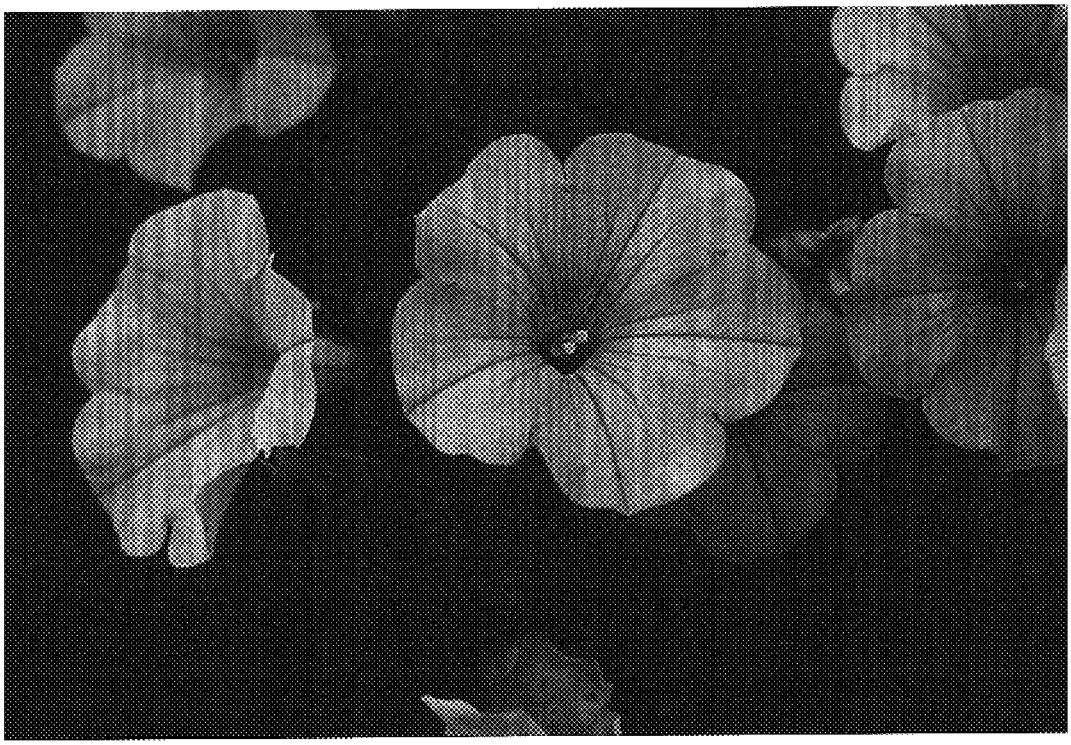
FIG. 2 shows a close view of the flowers of the new variety of Petunia plant 'Sunchiffon'.

*Venation.*—Generally radiates outwardly from the center and darker in coloration as illustrated in FIG. 2.

*Sepals.*—R.H.S. 146A on the upper surface and R.H.S. 147B on the under surface, generally lanceolate in configuration, with an entire margin, approximately 1.5 cm in length and approximately 3 mm in width at the widest point, and five in number. The calyx is tubular and divides into five sepals.

*Reproductive organs.*—1 normal pistil and 5 normal stamens. Color of pistil is vivid yellow-green (R.H.S. 144B, J.H.S. 3506). Color of stamens is yellowish-white (near R.H.S. 155D, J.H.S. 2501). The stigma is elliptical in configuration, R.H.S. 146D in coloration, and approximately 1 to 1.5 mm in length. The style is approximately 1.5 cm in length and R.H.S. 145C in coloration. The ovary is R.H.S. 143B in coloration. The stamens commonly range from 1.5 to 2 cm in length. Pollen is formed in a quantity that is typical of *Petunia hybrida* and is near R.H.S. 11D in coloration.

*Peduncle.*—Approximately 1.2 mm in diameter and approximately 1.5 cm in length. R.H.S. 146B in coloration. The texture is smooth.

*Seeds.*—R.H.S. 200B in coloration, approximately 0.7 mm in diameter, and generally round. The quantity is typical of *Petunia hybrida.*

*Physiological and ecological characteristics.*—High resistance to rain, cold, heat and diseases. Moderate resistance to pests.

This new variety of Petunia plant is most suitable for flower bedding and potting, particularly in hanging pots or in planters, and is excellent for use as a ground cover. Pinching of old blossoms will enhance the formation of new blossoms.

We claim:

1. A new and distinct variety of Petunia plant, substantially as herein illustrated and described, characterized particularly as to novelty by (A) having a decumbent growth habit with long stems, (B) abundant branching with a great profusion of blooms and the entire plant remaining in bloom for a considerable period of time, (C) flowers that are single and small in size, petals having a purplish-pink coloration with the base of the corolla throat being light greenish-yellow on the inside and the outside color of corolla tube being pale yellow, and (D) a high resistance to rain, heat, cold and diseases.

* * * * *